(12) United States Patent
Jacob

(10) Patent No.: US 8,257,761 B2
(45) Date of Patent: Sep. 4, 2012

(54) POLYPHENOL-CONTAINING PRODUCTS

(76) Inventor: Ludwig Manfred Jacob, Heldesheim am Rhein (DE)

( * ) Notice: Subject to any disclaimer, the term of this patent is extended or adjusted under 35 U.S.C. 154(b) by 50 days.

(21) Appl. No.: 12/638,192

(22) Filed: Dec. 15, 2009

(65) Prior Publication Data

US 2011/0142990 A1  Jun. 16, 2011

(51) Int. Cl.
*A23L 2/02* (2006.01)
(52) U.S. Cl. .............................. 426/51; 426/599; 435/72
(58) Field of Classification Search .................... 426/51, 426/599; 435/72
See application file for complete search history.

(56) References Cited

U.S. PATENT DOCUMENTS

2004/0235758 A1 * 11/2004 Setchell et al. ................. 514/27

OTHER PUBLICATIONS

Scalbert, A. et al. 2000. Dietary intake and bioavailability of polyphenols. J. Nutrition. 130: 2073S-2085S.*
Poyraxoglu, E. et al. 2002. Organic acids and phenolic compounds in pomegranates (*Punica granatum* L.) grown in Turkey. J. Fd. compositon and Anal. 15: 567-575.*

* cited by examiner

*Primary Examiner* — D Lawrence Tarazano
*Assistant Examiner* — Hamid R Badr
(74) *Attorney, Agent, or Firm* — Nixon & Vanderhye

(57) ABSTRACT

Fermentation product for adding to a food product, a food supplement or a diabetic food supplement. The product is obtained by fermentation of a medium containing pomegranate juice wherein the yeast *Saccharomyces boulardii* and *Lactobacillus plantarum* are used for the fermentation. The fermentation product contains 0.25% to 4% of one or more polyphenols, relative to the total weight of the ferment at the end of the fermentation process and before any optional other transformation, and the sugar content of the fermentation product, measured as percentage of glucose and of fructose, amounts to a maximum of 2% relative to the total weight of the ferment after the end of the fermentation process and before any optional other transformation.

13 Claims, No Drawings

POLYPHENOL-CONTAINING PRODUCTS

The invention relates to polyphenol-rich products of plants and also to a method of producing these products. In addition, the invention relates to the use of the polyphenol-containing products for producing foods, food supplements, dietetic foods and cosmetics; and also foods, food supplements, dietetic foods and cosmetics which contain such a product.

Polyphenols form a group of secondary plant components. They are ubiquitous in the plant kingdom with over 8000 compounds and can be derived in their basic structure from phenol (hydroxybenzene). The basic structure of polyphenols consists of an aromatic ring or ring system having two or more hydroxyl groups directly bound thereto. Polyphenols are taken to mean thereby aromatic compounds which contain at least two phenolic hydroxyl groups in the molecule. These include, in particular, the three dihydroxybenzenes (pyrocatechol, resorcinol, hydroquinone) and derivatives thereof. In nature, for example, free and etherified polyphenols occur in flower pigments (e.g. anthocyanins, anthocyanidins, flavones, flavonoids), in tanning agents (e.g. catechins, tannins), as lichen or fern components (e.g. usninic acid, acylpolyphenols), in lignins, as gallic acid derivatives, phloroglucin, pyrogallol or hexa-hydroxybenzene. In an acid environment the polyphenols are customarily readily water-soluble. They are highly susceptible to oxidation and in the course of polymerization and oxidation form brown precipitates. Taking into account their chemical structure, the poly-phenols comprise the groups of phenolcarboxylic acids, flavonoids, anthocyanins and anthocyanidins and stilbene derivatives. Polyphenols can occur in the form of relatively high-molecular-weight compounds such as, for example, glycosides or esters. Very frequently, polyphenols occur in plants as glycosides (bound to one or more identical or different sugar monomers) or as polymers.

The polyphenols are assigned to what are termed "secondary plant components", since they are not synthesized or metabolized in the primary metabolism of the plant. The exact biosynthetic and also metabolic pathways of the secondary plant components have not yet been completely elucidated. However, they have been proven to have hormonal (growth substances, steroids and pheromones) and protective character, wherein, in particular, protection against UV radiation, predators and fungal or bacterial infection can be mentioned. Some of the secondary plant components such as flavonoids and anthocyanins also contribute decisively to the color of flowers and/or fruits.

Numerous plants having a high content of polyphenols are known. These include, inter alia, plants familiar in Europe such as apples, tea, the leaves and grapes of red wine grapes, raspberries, strawberries, elderberries, sloes, blackcurrants and black cherries, and also less familiar plants and plant parts such as the skin and fruit flesh of mangosteen fruit (Garcinia mangostana), acai berries, amla berries, aronia berries, pomegranate, gingko, the seed of perilla (Perilla frutescens), black horehound, Chinese lemon balm and wild sesame. The polyphenols present in the plant occur quite predominantly as what are termed glycosides on one or more identical or different sugar molecules and/or as higher-molecular-weight polymers.

The increasing interest in polyphenols results from various in vivo and in vitro studies in which, inter alia, anticarcinogenic, antimutagenic, antioxidant, antiviral, antiproliferative, antithrombotic and lipid-lowering effects have been found.

The uptake of polyphenols into the body proceeds quite predominantly via absorption through the intestinal mucosa. In the process, in principle low-molecular-weight compounds can regularly pass through the intestinal mucosa very much better than higher-molecular-weight compounds. Since the plant polyphenols occur predominantly as glycosides or higher-molecular-weight polymers, for absorption of the polyphenols, first the sugar bonds of the glycosides must be cleaved and the pure polyphenols which are not bound to sugars (aglycones) released, or the higher-molecular-weight polymers of phenolic acids must be hydrolyzed.

This is performed in humans essentially by the large intestinal flora with a multiplicity of different enzymes. In part, glycosides are also already hydrolyzed in the small intestine by the enzyme lactase phlorizin hydrolase on the brush border of small intestinal cells. However, the small intestinal flora of about 5% of Europeans and about 90% of Africans and Asians are deficient in this enzyme. The beta-glucosidase of small intestinal cells which occurs, however, intracellularly (cytosolic), has a similar function to lactase phlorizin hydrolase. The majority of the glycosides therefore arrive uncleaved in the large intestine. Many glycosides therefore are first cleaved by the large intestinal microbiome, i.e. for example by specific glucosidases in the colon (Scalbert and Williamson, Dietary intake and bioavailability of polyphenols, J. Nutr. 2000 August; 130 (8S Suppl): 2073S-85S).

Polyphenols are therefore predominantly released from their glycosidic or polymeric form by the enzymes of the large intestinal flora. Numerous polyphenols in addition are subject to an enterohepatic circulation as glucuronides, methylates or sulfates which are in part likewise cleaved by the large intestinal microbiome.

The polyphenol aglycones released by metabolism in the large intestine not only have a lower molecular weight, but are also more lipophilic than the glycosides. For these reasons, the aglycones can pass through the hydrophobic cell membrane of the colocytes to a significant extent and are taken up into the blood circulation.

The bioavailability of the polyphenol aglycones is therefore particularly dependent on the metabolic activity of the large intestinal flora. A sufficient bioavailability of the polyphenols exists when an adequate large intestinal flora is present which firstly cleaves the sugar bond of the polyphenol glycosides and releases the polyphenol aglycones and secondly metabolizes the higher-molecular-weight polyphenol polymers to lower-molecular-weight components, and also possibly via a further biotransformation to still more lipophilic molecules additionally increases the bioavailability of the polyphenols. Only in the case of sufficiently high bioavailability are polyphenols taken up into the blood circulation in such an amount that a sufficiently high active substance concentration is achieved. Therefore, the biological activity of polyphenols is directly affected by the metabolic activity and composition of the large intestinal flora.

The composition and metabolic activity of the large intestinal microbiome, however, has great interindividual and also species-specific differences. For example the large intestinal microbiome of mice cannot ferment certain pomegranate polyphenols. Also in humans, considerable inter-individual differences result in the composition and metabolic activity of the intestinal flora. The bioavailability and therefore the biological activity of plant components, in particular also polyphenols, can therefore be very different for different persons.

Various processes are known in which plant components were also metabolically converted outside the human body. For instance, the rotting of fallen fruit is a biotransformation of components of the fallen fruit caused by microorganisms. Also, the production of wine or beer using wine yeast or brewer's yeast is such a process.

U.S. Pat. No. 5,639,496 A describes foods which were obtained by fermentation using *Saccharomyces boulardii*, in particular from cereals such as wheat and corn, soy and various vegetables such as, e.g., peas.

U.S. Pat. No. 5,891,440 describes, inter alia, the production of a skin cream from various plant components, including oil from pomegranate seed, coconut milk, Chinese asparagus and Schizandra berries. Some of the pomegranate seed oil can alternatively be replaced by a mixture of dry red wine, preferably Carmel Hilonim 1995 from the Carmel Winery, Israel, and with pomegranate seeds and juice fermented by wine yeast.

U.S. Pat. No. 6,953,574 B2 describes the fermentation of very different components of the most highly varied plants such as various types of vegetables or fruit, berries, herbs, fungi, nuts, and also animal products such as high-protein organs or apiary products, by most varied microorganisms such as bifidobacteria, acetic acid bacteria or propionic acid bacteria, yeasts, lactobacilli or else fungi. The most different hydrolyzed fermented media are obtained which contain metabolic products of various microorganisms to different extents. The field of use of the media which are generally described is reported to be very wide and is shown to comprise the treatment of virtually all diseases.

However, products which are of particular interest for adjuvant nutritional therapy, nutritional prevention, treatment and/or prophylaxis of diseases, are those which can be obtained by production processes using very specifically described and especially selected feedstocks, have a suitable spectrum of components and are therefore suitable specifically for use for general maintenance of health and also in certain diseases for adjuvant nutritional therapy and nutritional prevention.

The object of the present invention was therefore to provide a product having a high content of readily bioavailable polyphenols which is suitable in a nutritional dosage for producing foods, food supplements and also dietetic foods for general maintenance of health, in particular of heart, blood vessels and prostate, and in pharmacological dosage as medicament, in particular for adjuvant therapy and prevention of cancers (in particular prostate, breast, colon and/or lung carcinoma; in particular also in a supporting and synergistic manner in chemotherapy and/or radiation therapy), benign prostatic hyperplasia, arteriosclerotic blood vessel changes, coronary heart disease, cerebral sclerosis, hypercholesterolemia, chronic inflammatory diseases such as, e.g., rheumatoid arthritis, Alzheimer's disease, Parkinson's disease, multiple sclerosis and/or micro- and macroangiopathies in diabetes mellitus.

The object is surprisingly achieved by a fermentation product obtainable by a method comprising the fermentation of a fermentation batch containing pomegranate juice, wherein for the fermentation the yeast *Saccharomyces boulardii* and at least one species of lactobacilli selected from the group consisting of the species *Lactobacillus plantarum, Lactobacillus paraplantarum, Lactobacillus pentosus* and *Lactobacillus acidophilus* is used.

The pomegranate (fruit of the pomegranate tree, *Punica granatum*) is one of the oldest cultivated fruits and health fruits of mankind. In recent years the pomegranate has also returned to the focus of research. About 250 publications in recognized specialist scientific journals on the pomegranate have appeared to date. In vitro, in vivo and clinical studies have demonstrated convincing antioxidant, anti-inflammatory, antiarteriosclerotic and anticarcinogenic effects for pomegranate juice. In one study on 48 prostate cancer patients, with regular intake of pomegranate juice, inter alia, quadrupling of the doubling time of the blood level of the prostate cancer marker prostate-specific antigen (PSA) was found, which demonstrates great retardation of the progress of prostate cancer (Pantuck et al., Phase II Study of Pomegranate Juice for Men with Rising Prostate-Specific Antigen following Surgery or Radiation for Prostate Cancer, Clin. Cancer Res. 2006; 12, 13: 4018-4026). Other studies in an animal model and in vitro showed a pronounced growth-inhibitory effect for example against lung, bowel, skin and breast cancer for pomegranate juice. The intake of pomegranate juice in clinical studies significantly improved the circulation of the myocardium (heart muscle) in patients with coronary heart disease (CHD) and reduced arteriosclerotic deposits in the carotid artery (*Arteria carotis*). NF-kappaB- and TNF-alpha-mediated inflammatory processes and the development of Alzheimer's dementia were inhibited. Certain isolated compounds do not appear to be responsible therefor, but rather a synergistic interaction of various natural components of pomegranate. These modulate intracellular signal pathways and also gene expression and gene regulation.

Pomegranates have a very high content of certain secondary plant materials, the polyphenols. These include, in particular, phenol carboxylic acids (gallic acid, ellagic acid), polymerized derivatives thereof (especially ellagitannins, such as, e.g., punicalagin), flavonoids (such as for example catechin, quercetin, rutin), and also anthocyanins (such as delphinidin 3,5-diglucoside, delphinidin 3-diglucoside, cyanidin 3,5-diglucoside, cyanidin 3-glucoside, pelargonidin 3-glucoside).

It is known that certain pomegranate products can contain polyphenols, for example in the form of phenol carboxylic acids and polymers thereof and also flavonoids. The polyphenols of pomegranate are fundamentally predominantly in the form of glycosides or higher-molecular-weight polymers. Pomegranate products are offered to date either as pressed juice from pomegranate pulp or as dried extracts of the peel and membrane of pomegranates. For production thereof, mechanical, aqueous and/or alcoholic extraction routes are used. In all of these methods, however, the polyphenols remain in their sugar bond, i.e. exist as glycosides or are still present as higher-molecular weight-polymers in the pomegranate product. Their direct bioavailability is therefore low and first requires a biotransformation by the intestinal microbiome. At the same time, the bioavailability of the aglycones and/or lower-molecular-weight cleavage products depends very much on the individual large intestinal flora of the patient.

Thus in the sole and spectacular study to date with respect to oral use of pomegranate juice in prostate cancer patients it was found that although over 80% of the participants in the study responded to treatment with pomegranate juice ("responders"), this was demonstrated in a prolongation of the doubling time for the blood level of the prostate cancer marker PSA from a mean 15 months to a mean 54 months, which demonstrates a very significant retardation of the progress of the disease. However, among the responders there were significant differences in the expression of this effect. This is reflected in the great width of variation of the PSA doubling time achieved of 54±102 months. In some of the patients, only a slight retardation of the increase of the PSA blood level was achieved, whereas in 35% of the patients there was even an absolute decrease in the PSA blood level. In 9% of the patients, a decrease of the PSA level by more than 50% was observed (Pantuck et al., 2006). This high width of variation in the effect of pomegranate juice cannot be explained by possible differences in the prostate carcinomas alone, but is also due to differences between individuals in the bioavailability of the pomegranate polyphenols. This is impressively demonstrated by a bioavailability study using pomegranate polyphenols. After oral intake it was found that the serum concentrations of the active substances varied greatly between different persons and the metabolites studied did not appear at all in the blood in one-third of the subjects. This phenomenon was primarily due to the individual composition of the large intestinal flora (Cerdá et al., J. Agric. Food Chem. 2005 Jul. 13; 53 (14): 5571-6).

It is certain that the biological effect of the pomegranate juice is largely due to the aglycone metabolites of the intestinal flora resulting from the glycosidic and polymeric polyphenols, and not to a direct effect of the glycosidic and polymeric polyphenols present in the juice. This is also supported by the results of the bioavailability studies.

In addition, it appears that the special effect of pomegranate juice is not due to one or a few individual substances, but to the synergistic action of a spectrum of components (L. M. Jacob, Granatapfel: Prävention and adjuvante Ernährungstherapie bei Krebserkrankungen [Pomegranate: Prevention and Adjuvant Nutritional Therapy in Cancers], EHK 2007 (56): 464-473). Overall no individual specific pharmacological mechanism of action appears to be present, but rather a positive nutritional effect of pomegranate juice.

In particular, various aglycone polyphenols also appear to participate in the activity which are only formed or released by biotransformation and/or deglycosylation of pomegranate components and thereby become bioavailable.

In order to provide a product having a high content of readily bioavailable polyphenols, according to the invention, therefore, not only is pomegranate juice used as a polyphenol-rich starting product, but components present therein are additionally biotransformed and made bioavailable first by fermentation with suitable microorganisms—occurring outside the human body. This enables persons having individual intestinal flora less suitable for this also to profit from the active polyphenol metabolites.

According to the invention, the yeast *Saccharomyces boulardii* and at least one species of *lactobacilli* selected from the group consisting of the species *Lactobacillus plantarum, Lactobacillus paraplantarum, Lactobacillus pentosus* and *Lactobacillus acidophilus* are used for the fermentation.

The yeast *Saccharomyces boulardii* belongs to the genus *Saccharomyces* and was first detected in 1923 in Indochina by Henri Boulard on the peel of lychee fruits. The presence of the yeast *Saccharomyces boulardii* in the gastrointestinal tract is harmless to humans. It is used, inter alia, in freeze-dried form in capsules for the treatment of diarrhea and for restoration of the intestinal flora after oral intake of antibiotics, wherein it presumably inhibits in the intestine the growth of other pathogens which could cause diarrhea, at least temporarily by its own strong growth. *Saccharomyces boulardii*, in contrast to typical wine yeasts, has an unusually high optimum growth temperature of 37° C. (Mansour-Ghanaei et al., World J Gastroenterol 2003 August; 9 (8): 1832-1833; McFarland et al., Microbial Ecology in Health and Disease 1993 Jul. 6 (4): 157-171).

Lactobacilli are among the Gram-positive bacteria. They can generate lactic acid by fermentation and are generally non-pathogenic to humans. Some species of lactobacilli are used in food production, for example in the production of milk products. Lactobacilli can, however, also occur as nuisances in the food industry and cause unwanted reactions, such as, for example, in brewing. Some lactobacilli form a part of the natural bacterial flora of humans, in particular of the gastrointestinal tract. For instance, *Lactobacillus plantarum*, for example, can also occur in the gastrointestinal tract of humans. Lactobacilli tolerate in general low pHs better than related genera, such as, for example, pediococci, and also grow at pHs of, for example, 4-5.

In contrast to conventional use fermentations of fruits using wine yeast used for producing alcohol which—corresponding to the temperature optimum of the wine yeast used for alcohol production—proceed at moderate temperatures of 10-25° C., in the production of the polyphenol-containing fermentation product according to the invention it has surprisingly proved to be particularly advantageous to use a culture temperature of 30-38° C. during the fermentation. It has been found that the required enzymatic reactions, e.g. for the depolymerization and deglycosylation proceed most effectively at these temperatures. The use of *Saccharomyces boulardii* has therefore surprisingly proved to be particularly advantageous according to the invention, since this yeast prefers particularly high temperatures of above 30° C. for optimum growth. In addition, it has surprisingly been proven that the bacterium *Lactobacillus plantarum*, and also *Lactobacillus paraplantarum, Lactobacillus pentosus* and *Lactobacillus acidophilus*, are suitable for the fermentation of pomegranate juice, with low-molecular-weight polyphenols being obtained. These lactobacilli obviously have their own set of enzymes. However, at the start of the fermentation a sufficient microbial concentration of lactobacilli must be used and favorable growth conditions (temperature, pH, sugar content) of the solution must be ensured, since pomegranate juice contains antibacterial polyphenols which inhibit the bacterial growth. The enzyme set of these lactobacilli in addition supplements the enzyme set of the yeast *Saccharomyces boulardii* in a particularly suitable manner for producing the fermentation product according to the invention in the context of a co-fermentation.

By means of the fermentation with *Saccharomyces boulardii* and *Lactobacillus plantarum/paraplantarum/pentosus/acidophilus*, the intestinal digestion process is reproduced outside the body in a certain manner, and so improved bioavailability of the pomegranate polyphenols is also achieved in persons having an unsuitable intestinal flora. Such whole pomegranate products having low-molecular-weight polyphenol metabolites, which were fermented in an intestinal-like environment, are not currently known.

Such a fermented pomegranate product is very suitable for general cell protection and for maintaining cell health, in a pharmacological dose also as a medicament which is suitable for adjuvant therapy and prevention of cancers (in particular prostate, breast, colon and/or lung cancer, in particular also in a supporting and synergistic manner in chemotherapy and/or radiation therapy), benign prostatic hyperplasia, arteriosclerotic blood vessel changes, coronary heart disease, cerebrosclerosis, hypercholesterolemia, chronic inflammatory diseases, such as, e.g., rheumatoid arthritis, Alzheimer's disease, Parkinson's disease, multiple sclerosis and/or micro- and macroangiopathies in diabetes mellitus.

The fermentation products according to the invention can, in addition, be obtained with a significantly reduced sugar content compared with the natural sugar content of pomegranate juice. This enables, for example, diabetics also to profit from the fermented pomegranate polyphenols. For diabetics this is of particular interest since for them there is a greatly increased risk of micro- and macroangiopathies compared with the average of the population, which risk can be reduced in a nutritional manner by the pomegranate polyphenols, as shown in studies. The spectrum of components apparently required therefor is predominantly present in pomegranate pulp which, however, is of high sugar content and therefore of restricted suitability for diabetics without prior reduction of the sugar content. Using the fermentation product according to the invention enables the natural sugar content of the pomegranate juice to be greatly reduced, but at the same time a large bandwidth of natural components of the pomegranate pulp and derivatives thereof may be obtained.

The fermentation products according to the invention preferably have a sugar content, measured as a fraction of glucose and fructose, of in total a maximum of 2% by weight, based on the total weight of the fermentation batch after the end of the fermentation process and before any further processing. Particularly preferably, the fermentation products according to the invention have a sugar content of in total a maximum of 1% by weight, very particularly preferably of a maximum of 0.25% by weight, measured as a fraction of glucose and fructose and based on the total weight of the fermentation batch after the end of the fermentation process and before any further processing.

The fermentation products according to the invention preferably contain 0.25 to 4% by weight of one or more polyphenols, based on the total weight of the fermentation batch after the end of the fermentation process and before any further processing. Particularly preferably, the fermentation products according to the invention contain 0.5 to 3% by weight, very particularly preferably 0.7 to 2.5% by weight, of one or more polyphenols, in each case based on the total weight of the fermentation batch after the end of the fermentation process and before any further processing. A very low polyphenol content can restrict the efficacy and nutritional quality of the fermentation product. In the case of a very high polyphenol content, unwanted strong antimicrobial activity can occur in the fermentation batch, which makes fermentation impossible. The content of polyphenols is determined by the Folin-Ciocalteu method usual in the wine and juice industry, using gallic acid as reference substance.

Preferably, in the fermentation product according to the invention, there is a higher fraction of polyphenols having a lower molecular weight present than in the fermentation batch at the start of the fermentation. The molecular weight of the polyphenols can be determined, for example, by means of mass spectrometry after prior HPLC separation.

Preferably, the fermentation product according to the invention contains polyphenols selected from the group consisting of gallic acid and/or derivatives of gallic acid (e.g. gallotannins); ellagic acid and/or derivatives and/or metabolites of ellagic acid and of ellagitannins; flavonoids such as, for example, quercetin and/or metabolites and/or derivatives of flavonoids, anthocyans and/or anthocyanidins.

Particularly preferably, the fermentation product according to the invention contains ellagic acid, derivatives of ellagic acid, ellagic acid metabolites and/or ellagitannins.

Preferably, the polyphenols contained in the fermentation product according to the invention have a significantly reduced fraction of glycosylated compounds.

The various polyphenols can be separated from one another and identified by, for example, chromatographic methods, such as, e.g., HPLC or else a combination of HPLC and mass spectrometry.

The invention further relates to a method of producing a fermentation product, comprising the fermentation of a fermentation batch containing pomegranate juice, wherein for the fermentation the yeast Saccharomyces boulardii and at least one species of lactobacilli selected from the group consisting of the species Lactobacillus plantarum, Lactobacillus paraplantarum, Lactobacillus pentosus and Lactobacillus acidophilus is used.

For the fermentation, the yeast Saccharomyces boulardii and at least one species of lactobacilli selected from the group consisting of the species Lactobacillus plantarum, Lactobacillus paraplantarum, Lactobacillus pentosus and Lactobacillus acidophilus is used. In particular a co-fermentation using the yeast Saccharomyces boulardii and at least one species of lactobacilli selected from the group consisting of the species Lactobacillus plantarum, Lactobacillus paraplantarum, Lactobacillus pentosus and Lactobacillus acidophilus, is a method of the invention.

The fermentation can proceed generally either first in the presence of the yeast Saccharomyces boulardii and subsequently thereto in the presence of at least one species of lactobacilli selected from the group consisting of the species Lactobacillus plantarum, Lactobacillus paraplantarum, Lactobacillus pentosus and Lactobacillus acidophilus; or first in the presence of at least one species of lactobacilli selected from the group consisting of the species Lactobacillus plantarum, Lactobacillus paraplantarum, Lactobacillus pentosus and Lactobacillus acidophilus, and subsequently thereto in the presence of the yeast Saccharomyces boulardii; or as a co-fermentation in the simultaneous presence of the yeast Saccharomyces boulardii and at least one species of lactobacilli selected from the group consisting of the species Lactobacillus plantarum, Lactobacillus paraplantarum, Lactobacillus pentosus and Lactobacillus acidophilus.

Preferably the fermentation is carried out as a co-fermentation in the simultaneous presence of the yeast Saccharomyces boulardii and at least one species of lactobacilli selected from the group consisting of the species Lactobacillus plantarum, Lactobacillus paraplantarum, Lactobacillus pentosus and Lactobacillus acidophilus.

In a further preferred embodiment, after an initial fermentation of about 1-3 days with Saccharomyces boulardii or another suitable microorganism, subsequently at least one species of lactobacilli selected from the group consisting of the species Lactobacillus plantarum, Lactobacillus paraplantarum, Lactobacillus pentosus and Lactobacillus acidophilus is added for further fermentation.

Preferably, among the lactobacilli, the species Lactobacillus paraplantarum is selected.

Likewise preferably, among the lactobacilli the species Lactobacillus plantarum is selected.

Preferably, the fermentation proceeds as a co-fermentation in the simultaneous presence of the yeast Saccharomyces boulardii and Lactobacillus plantarum. Very particularly preferably the fermentation proceeds as a co-fermentation in the simultaneous presence of the yeast Saccharomyces boulardii and Lactobacillus paraplantarum.

For the fermentation, for example, microbial concentrations of $2 \times 10^9$-$2 \times 10^{11}$ microbes of Saccharomyces boulardii per 10 l of fermentation batch and/or $2 \times 10^{10}$-$2 \times 10^{13}$ microbes of the lactobacilli per 10 l of fermentation batch can be used. Optionally, first an inoculum is prepared having an elevated microbe concentration which is then added to the remaining fermentation batch.

For the fermentation, in addition, one or more other species of microorganisms which are different from the species mentioned (Saccharomyces boulardii, Lactobacillus plantarum, Lactobacillus paraplantarum, Lactobacillus pentosus and Lactobacillus acidophilus) can additionally be used. For example, in addition to Saccharomyces boulardii and Lactobacillus plantarum, Lactobacillus paraplantarum, Lactobacillus pentosus and Lactobacillus acidophilus, one or more species of wine yeast (e.g. Saccharomyces cerevisiae, Saccharomyces ellipsoides, Saccharomyces uvarum, Saccharomyces bayanus, Zygosaccharomyces) such as champagne yeast, port wine yeast, Bordeaux yeast, Burgundy yeast or sherry yeast and/or nutritionally harmless fungi such as, e.g., *Aspergillus oryzae* can additionally be added to the fermentation batch.

The pomegranate juice can be obtained by expressing the comminuted fruits. For example, the peeled fruits can be dejuiced using a dejuicer of the Champion brand from Plastaket Manufacturing Co. (Lodi 95240, California, USA; German importer: Keimling Naturkost GmbH, 21614 Buxtehude). The pomegranate juice can also be obtained from the fruits in other suitable ways. Preferably, the pomegranate juice is obtained from peeled pomegranates.

The fermentation batch can also contain at least one other component of the pomegranate, for example leaves, juice concentrate, puree, peels, white separation membranes, blossoms and/or extracts thereof. Leaves are taken to mean the green leaves of the pomegranate tree. White separation membranes are taken to mean the white separation walls which enclose the seeds enclosed by the red fruit flesh. Blossoms are taken to mean the red blossoms of the pomegranate tree.

The fermentation batch can, in addition to pomegranate juice, also contain fruit juice and/or fruit components of one or more plants, preferably selected from the group consisting of red grapes, acai berries, amla berries, aronia berries, raspberries, strawberries, elderberries, sloes, blackcurrants and black cherries.

The fermentation batch, at the start of the fermentation, preferably has a sugar content, measured as fraction of glucose and fructose, of in total 8-17% by weight, particularly preferably of 13-15% by weight, in each case based on the total weight of the fermentation batch at the start of the fermentation. If the sugar content is too low, in the fermentation batch there are insufficient nutrients for the microorganisms used. If the sugar content is too high, considerable production of alcohol can occur, which likewise can have a growth-inhibitory action on yeast and lactobacilli and, possibly, other microorganisms used.

The fermentation batch preferably has a pH of 3 to 6, particularly preferably of 4 to 5. The pH of the fermentation batch can, for example, be set by adding sodium hydrogencarbonate, calcium carbonate and/or potassium carbonate and optionally can be corrected during the fermentation process. Acidification of the fermentation batch is generally not necessary, but can be carried out, if required, for example by addition of sodium citrate. If the pH of the fermentation batch is too high or too low, growth and metabolism of the microorganisms used are not optimal for producing the fermentation product according to the invention.

The fermentation batch denotes the aqueous mixture which is either present at the start of the fermentation and contains pomegranate juice, the yeast *Saccharomyces boulardii* and/or at least one species of lactobacilli selected from the group consisting of the species *Lactobacillus plantarum, Lactobacillus paraplantarum, Lactobacillus pentosus* and *Lactobacillus acidophilus*, and also optionally other components, or else the aqueous mixture which is formed therefrom during and after the fermentation by the fermentation process.

The fermentation proceeds preferably at a temperature of 30-38° C., particularly preferably 35-37° C., of the fermentation batch. If the temperature of the fermentation batch is too high or too low, growth and metabolism of the microorganisms used are not optimal for the production of the fermentation product according to the invention.

The fermentation proceeds preferably for a time period of 3 to 8 days, particularly preferably 4 to 6 days. The end point of the fermentation is customarily achieved when, owing to the sugar content of the fermentation batch which is reduced by metabolic activity of the microorganisms, the carbon dioxide production by the microorganisms used has greatly decreased and is scarcely still observed or is no longer observed at all.

The fermentation can be followed by one or more further process steps, preferably a pasteurization, a lyophilization and/or a micellization into liposomes.

If the fermentation product is intended to contain dead microorganisms, preferably pasteurization and optionally further process steps then follow. If the fermentation product should contain microorganisms which are still living, preferably a pasteurization is omitted. A pasteurization can be carried out by the suitable methods which are known to those skilled in the art. For example, the pasteurization can be carried out by short-time heating of the fermentation product to 60-90° C. In a possible variant, the fermentation product can be heated for some seconds to about 85° C. for pasteurization. Preferably, the fermentation product contains dead microorganisms.

In a preferred embodiment, the fermentation is followed, after a pasteurization, by a lyophilization of the fermentation product. After the lyophilization the fermentation products according to the invention preferably contain 10 to 30% by weight, still more preferably 15 to 25% by weight, based on the lyophilizate, of one or more polyphenols. The content of polyphenols is determined by the Folin-Ciocalteu method familiar in the wine and juice industry using gallic acid as reference substance and after reconstituting the lyophilizate in distilled water. The lyophilization can be carried out by the suitable methods known to those skilled in the art. Commercially available industrial freeze dryers can be used for the lyophilization. Preferably, no cryoprotective aids or carrier substances are added for the lyophilization.

A micellization into liposomes increases the lipophilicity of the end product. Preferably, a lyophilization of the fermentation product proceeds before micellization into liposomes. The micellization into liposomes can be carried out by the suitable methods known to those skilled in the art. Suitable phospholipids can be used, for example, as liposome-forming amphiphilic compounds.

Other substances can be added to the fermentation batch or to the fermentation product before or after any pasteurization, lyophilization and/or micellization into liposomes. For example, one or more of the substances selected from the group consisting of tributyrin, butyrate, curcumin and pomegranate seed oil can be added. Said substances can induce, in a similar manner to the pomegranate polyphenols, the redifferentiation of cancer cells and are preferably used in an amount such that a substance concentration sufficient for this activity is present in the end product.

Carrying out the fermentation industrially has no special peculiarities, but it can proceed according to the methods which are known to those skilled in the art and are suitable. For example, the fermentation can be carried out in a suitable container having a $CO_2$ outlet valve with exclusion of oxygen. If a deposit occurs towards the end of the fermentation, occasional stirring of the fermentation batch can be carried out.

The fermentation products obtained by one or more of the above-described methods are likewise subject matter of the invention.

A further subject matter of the invention is the use of the fermentation product according to the invention for producing a food, a food supplement, a dietetic food or a cosmetic. Preferably, the fermentation product according to the invention is used for producing a food, a food supplement or a dietetic food. Very particularly preferably, the fermentation product according to the invention is used for producing a food supplement.

Medicaments are taken to mean agents which have the intended purpose of healing, ameliorating, preventing or recognizing diseases, suffering or bodily harm, or which have the nature of affecting the state or the function of the body or mental states, and have a predominantly pharmacological action. Foods are not medicaments.

In contrast, food supplements and dietetic foods are considered to be foods. Foods are substances which are intended to be consumed by humans in the unchanged or processed state, except for substances which are predominantly intended for purposes other than nutrition or pleasure. Foods therefore have a predominantly nutritional action. Dietetic foods are intended for a special nutrition and correspond to special nutritional requirements of consumers whose digestive or absorptive process or metabolism is disturbed or who are in special physiological states or are healthy infants or small children. Food supplements are differentiated from the dietetic foods in that food supplements do not serve a particular nutritional purpose, but supplement general nutrition, e.g. as a concentrate of nutrients or other substances having specific nutritional or physiological activity.

Cosmetics are substances or preparations of substances which are intended to be used exclusively or predominantly externally on the human body or in the oral cavity thereof for cleaning (e.g. soaps, hair shampoos, dentifrices), for protection, for maintaining a good state (e.g. skin creams, lotions) for perfuming, for changing the appearance (e.g. tanning agents, hair dyes) and/or for affecting body odor (e.g. deodorant sticks). These can therefore be products for external application such as, for example, salves, creams or spray solutions.

If medicaments are produced using the fermentation product according to the invention, these can be medicaments for internal or external use. Preference in this case is given to an agent for internal use, particularly preferably for peroral or rectal use.

The foods, food supplements and dietetic foods produced using the fermentation product according to the invention are agents for internal use. Particularly preferably, the fermentation products according to the invention are used for producing food supplements and dietetic foods for peroral use.

The foods, food supplements, dietetic foods, medicaments or cosmetics produced using the fermentation products according to the invention can have various administration forms. Preferably, the food supplements, dietetic foods, medicaments or cosmetics produced using the fermentation products according to the invention are agents in the form of drops, a juice, a liquid concentrate, a solution, an elixir, capsules, tablets, dragées, pastilles, globules, a granulate, ampoules, suppositories, enemas, a powder or effervescent tablets or a means for external application, for example as a salve, cream or spray solution. Particularly preferably they are agents in the form of a powder or capsules.

Preferably, in the case of a nutritional dose of the fermentation product, this concerns a food supplement or dietetic food for general health maintenance, in particular of heart, blood vessels and prostate; or in the case of pharmacological dose this concerns a medicament which is suitable in particular for adjuvant therapy and prevention of cancers (in particular prostate, breast, colon and/or lung cancers; in particular also in a supporting and synergistic manner in chemotherapy and/or radiation therapy), benign prostatic hyperplasia, arteriosclerotic blood vessel changes, coronary heart disease, cerebrosclerosis, hypercholesterolemia, chronic inflammatory disorders such as, for example, rheumatoid arthritis, Alzheimer's disease, Parkinson's disease, multiple sclerosis and/or micro- and macroangiopathies in diabetes mellitus.

The invention further relates to foods, food supplements, dietetic foods or cosmetics which contain a fermentation product according to the invention and/or a fermentation product obtained by the method according to the invention.

Hereinafter the invention is described in more detail by exemplary embodiments.

EXEMPLARY EMBODIMENT 1

First, two inocula are prepared:
Inoculum 1: *Saccharomyces boulardii*
1 g of *Saccharomyces boulardii* ($2\times10^{10}$ lyophilized microbes; obtainable commercially, for example in pharmacies) is inoculated into 1 liter of pomegranate juice at 36° C. for 24 h.
Inoculum 2: *Lactobacillus plantarum*
0.5 g of *Lactobacillus plantarum* ($2\times10^{11}$ lyophilized microbes; commercially obtainable, for example from Danisco) is inoculated into 1 liter of a mixture of 300 ml of water and 700 ml of pomegranate juice at a pH of about 5 for 24 h at 36° C.

Then, the fermentation batch is produced and the fermentation is carried out. For this the two inocula are mixed in a suitable fermentation vessel having a $CO_2$ outlet valve with 10 l of pomegranate juice which can be obtained, e.g., by juicing the peeled fruits using a juicer of the Champion brand from Plastaket Manufacturing Co. (Lodi 95240, California, USA; German importer: Keimling Naturkost GmbH, 21614 Buxtehude). The pomegranate juice should have a sugar content of approximately 14 g/l (total content of glucose and fructose). The pH of the fermentation batch is set to pH 4.5 using sodium hydrogencarbonate or potassium carbonate. The fermentation batch is fermented for about 4-5 days at a temperature of 36° C. with exclusion of oxygen until the sugar content has decreased to less than 0.5% (5 g/l) and the $CO_2$ production has ceased.

The resultant fermentation product is preferably pasteurized and freeze dried or else, less preferably, freeze dried without pasteurization containing the living microbes.

EXEMPLARY EMBODIMENT 2

Inoculum 2 (*Lactobacillus plantarum*) of exemplary embodiment 1 is mixed in a suitable fermentation vessel having a $CO_2$ outlet valve with 10 l of pomegranate juice which can be obtained, e.g., by juicing the peeled fruits using a juicer of the Champion brand from Plastaket Manufacturing Co. (Lodi 95240, California, USA; German importer: Keimling Naturkost GmbH, 21614 Buxtehude). The pomegranate juice should have a sugar content of approximately 14 g/l (total content of glucose and fructose). The pH of the fermentation batch is set to pH 4.5 using sodium hydrogencarbonate or potassium carbonate. The fermentation batch is fermented for about 24 h at a temperature of 36° C. in the absence of oxygen. Thereafter inoculum 1 (*Saccharomyces boulardii*) of exemplary embodiment 1 is added. The fermentation is continued for about 4-5 days at a temperature of 36° C. in the absence of oxygen until the sugar content has fallen to below 0.5% (5 g/l) and the $CO_2$ production has ceased.

The resultant fermentation product is preferably pasteurized and freeze dried or, less preferably, freeze dried without pasteurization containing the living microbes.

The invention claimed is:
1. A fermented pomegranate juice obtained by a method comprising the fermentation of a medium containing pome- granate juice, wherein the yeast *Saccharomyces boulardii* and *Lactobacillus plantarum* are used for the fermentation, wherein the fermented pomegranate juice contains 0.25% to 4% of one or more polyphenols, relative to the total weight of the fermented pomegranate juice at the end of the fermentation process and before any optional other transformation;

the sugar content of the fermented pomegranate juice, measured as percentage of glucose and of fructose, amounts to a maximum of 2% relative to the total weight of the fermented pomegranate juice after the end of the fermentation process and before any optional other transformation;

wherein the fermentation is first carried out in the presence of the yeast *Saccharomyces boulardii* and immediately afterward in the presence of *Lactobacillus plantarum* or wherein the fermentation is first carried out in the presence of *Lactobacillus plantarum* and immediately afterward in the presence of the yeast *Saccharomyces boulardii*; or wherein the fermentation takes place as a cofermentation in the simultaneous presence of the yeast *Saccharomyces boulardii* and *Lactobacillus plantarum*;

wherein the fermented pomegranate juice has a pH value of 3 to 6 and wherein the fermentation takes place at a temperature of from 30 to 38° C.

2. A method for the production of a fermented pomegranate juice as claimed in claim 1, comprising the fermentation of a medium containing pomegranate juice, wherein the yeast *Saccharomyces boulardii* and *Lactobacillus plantarum* are used for the fermentation.

3. The method as claimed in claim 2, wherein the fermentation takes place at a temperature of from 35 to 37° C.

4. The method as claimed in claim 2, wherein the medium contains at least one other pomegranate component selected from the group consisting of leaves, juice concentrate, puree, peel, white membranes, flowers and extracts thereof.

5. The method as claimed in claim 2, wherein the medium contains fruit juice and/or fruit components of one or more plants.

6. The method as claimed in claim 5, wherein the medium contains fruit juice and/or fruit components selected from the group consisting of black grapes, acai berries, Indian gooseberries, aronia berries, raspberries, strawberries, elderberries, sloes, blackcurrant and black cherries.

7. The method as claimed in claim 5, wherein the fermented pomegranate juice has a pH value of 4 to 5.

8. The method as claimed in claim 2, wherein, at the beginning of the fermentation, the medium has a sugar content, calculated as percentage of glucose and of fructose, of from 8% to 17% relative to the total weight of the medium.

9. The method as claimed in claim 8, wherein, at the beginning of the fermentation, the medium has a sugar content, calculated as percentage of glucose and of fructose, of from 13% to 15% relative to the I total weight of the medium.

10. The method as claimed in claim 2, wherein the fermentation is followed by one or more other steps.

11. The method as claimed in claim 10, wherein the fermentation is followed by a pasteurization, a lyophilization and/or a micellar transformation to liposomes.

12. The method of producing a food product, food supplement, dietetic food product or cosmetic product comprising adding a fermented pomegranate juice as claimed in claim 1 to a food product, a food supplement, a dietetic food product or a cosmetic product.

13. A food product, a food supplement, a dietetic food product or a cosmetic product, containing a fermented pomegranate juice as claimed in claim 1.

\* \* \* \* \*